(12) United States Patent
Goodenough et al.

(10) Patent No.: US 9,934,603 B2
(45) Date of Patent: Apr. 3, 2018

(54) THREE-DIMENSIONAL RESOLUTION GAUGE FOR EVALUATING PERFORMANCE OF TOMOGRAPHIC IMAGING SYSTEMS

(71) Applicant: THE PHANTOM LABORATORY, INCORPORATED, Greenwich, NY (US)

(72) Inventors: David J. Goodenough, Myersville, MD (US); Joshua R. Levy, Salem, NY (US)

(73) Assignee: THE PHANTOM LABORATORY, INCORPORATED, Greenwich, NY (US)

( * ) Notice: Subject to any disclaimer, the term of this patent is extended or adjusted under 35 U.S.C. 154(b) by 0 days.

(21) Appl. No.: 15/097,515

(22) Filed: Apr. 13, 2016

(65) Prior Publication Data

US 2016/0314570 A1     Oct. 27, 2016

Related U.S. Application Data

(60) Provisional application No. 62/150,961, filed on Apr. 22, 2015.

(51) Int. Cl.
| | |
|---|---|
| *G06K 9/00* | (2006.01) |
| *G06T 15/08* | (2011.01) |
| *G06T 11/00* | (2006.01) |
| *A61B 6/00* | (2006.01) |

(52) U.S. Cl.
CPC .............. *G06T 15/08* (2013.01); *A61B 6/583* (2013.01); *G06T 11/008* (2013.01); *G06T 2211/40* (2013.01)

(58) Field of Classification Search
CPC ............................ G06T 2211/40; A61B 6/583
See application file for complete search history.

(56) References Cited

U.S. PATENT DOCUMENTS

| | | | | |
|---|---|---|---|---|
| 4,613,819 A | * | 9/1986 | Chui | ...................... G01R 33/58 324/300 |
| 5,164,978 A | * | 11/1992 | Goodenough | ......... A61B 6/583 250/252.1 |
| 5,600,574 A | | 2/1997 | Reitan | |
| 5,841,835 A | | 11/1998 | Aufrichtig et al. | |
| 6,231,231 B1 | | 5/2001 | Farrokhnia et al. | |
| 6,720,766 B2 | | 4/2004 | Parker et al. | |
| 6,813,374 B1 | | 11/2004 | Karimi et al. | |
| 7,085,430 B2 | | 8/2006 | Winsor et al. | |
| 7,286,631 B2 | | 10/2007 | Li et al. | |
| 7,522,756 B2 | | 4/2009 | Bueno et al. | |

(Continued)

*Primary Examiner* — Oneal R Mistry
(74) *Attorney, Agent, or Firm* — Heslin Rothenberg Farley & Mesiti P.C.

(57) ABSTRACT

A three-dimensional resolution gauge for evaluating performance of a tomographic imaging system includes a series of groupings of 3-dimensional line pairs. All of the line pairs are oriented at a common set acute angle relative to a reference x-y imaging plane. The frequency of the line pairs of respective groupings of the series vary from highest density to lowest density corresponding to fine resolution and coarse resolution, respectively. Imaging of the series of groupings by the tomographic imaging system provides, in a single scan, a simultaneous visualization of combined effects of x-y in-plane resolution and slice thickness z direction resolution.

18 Claims, 6 Drawing Sheets

(56) References Cited

U.S. PATENT DOCUMENTS

| | | |
|---|---|---|
| 7,812,605 B2 | 10/2010 | Schilling |
| 8,308,362 B2 | 11/2012 | Dove et al. |
| 8,348,508 B2 | 1/2013 | Goodenough et al. |
| 2005/0281478 A1* | 12/2005 | Kaufman .............. G06F 19/321 382/260 |
| 2008/0217561 A1* | 9/2008 | Mackie ................ A61N 5/1048 250/492.3 |
| 2011/0229055 A1* | 9/2011 | Clarke .................. A61B 6/583 382/287 |

* cited by examiner

THREE-DIMENSIONAL RESOLUTION GAUGE FOR EVALUATING PERFORMANCE OF TOMOGRAPHIC IMAGING SYSTEMS

CROSS-REFERENCE TO RELATED APPLICATION

This application claims priority of Provisional Application No. 62/150,961, filed on Apr. 22, 2015, the entire contents of which is hereby incorporated by reference herein.

FIELD OF THE INVENTION

This invention relates, in general, to a phantom for evaluating performance of a tomographic imaging system and, more particularly, to a three-dimensional resolution gauge that provides, via a single scan of a single test object, a simultaneous visualization of combined effects of x-y in-plane resolution and slice thickness z direction resolution.

BACKGROUND ART

The growing trend toward 3D imaging involving Volume Computed Tomography (CT) scanners and the use of 3D and Multi Planar Reconstruction (MPR) techniques leads to the need for phantoms and test methods that reveal to the radiologist and physicist actual 3D resolution, i.e., measures involving not only in-plane (x,y) resolution and related Modulation Transfer Functions (MTF's) but also slice width and Slice Sensitivity Profiles (SSP). These "combined" effects can be visualized and studied with the new resolution gauge of the present invention and are also amenable to analysis by automated approaches.

Resolution gauges have a long history of use in both photographic and radiological imaging. Repetitive patterns of contrasting bars and spaces (line pairs) at increasing frequency (repetition rates) are presented for visual (or computer) analysis for the observer to choose the pattern where no surviving contrast between the bars and spaces is perceived. In classical photography or TV images, the display image is basically a 2-D image (x,y plane) and therefore typical resolution gauges are also 2-D and, although usually arranged in a linear direction, can be arranged in other geometric presentations within the 2-D image space.

In CT, the images which are usually shown as 2D images, actually represent a set of given x,y (2D) information sets as results from averaging of all the 2-D planes within the z cut (slice width) of information. As such, there is a hidden or masked dimension (z) in the conventional 2D display of a 3D (x,y,z) acquisition of CT data. The Phantom Laboratory of Salem, N.Y. has produced CT resolution gauges that have a very thin (z-axis) extent, or maintained the periodic patterns of the resolution gauge constant in the z-axis direction, so that essentially the z-axis thickness had no effect on the perceived resolution or repetition rate. See for example, U.S. Pat. No. 5,164,978. Although this works well if one is interested in the resolution of an "infinitely thin" slice, it would not represent resolution aspects of the image when limited by the actual z-axis (slice thickness) cut.

In practice, most anatomical structures have variation in x,y, and z axis of the patient. Thus, current CT resolution gauges, in deliberately ignoring or minimizing the z-axis effect of the gauge, could tend to mislead the physician or observer to think that the resolution as seen from the gauge represents the resolution as might be achieved in the actual patient anatomy on a corresponding CT scan, rather than just in the 2D resolution gauge.

A typical axiom in imaging is that the smallest size object that might be seen from a given image of a resolution gauge is approximately, $d \sim 1/(2\ fc)$ where fc is the cutoff frequency, and d represents line spacing, thus a 0.5 mm object can usually be seen with a spatial frequency cutoff (fc) of 1 line pair/mm.

In the event that an object is "averaged" in a given slice thickness, the perceived contrast would be reduced and the smallest object that might be perceived would be considerably higher.

SUMMARY OF THE INVENTION

In order to address this important issue of 3D resolution in CT (and other tomographic) scans as involving not only x,y, resolution but also, z axis effects, a new gauge has been developed that not only reflects periodic pattern(s) of increased frequency in the x,y plane but extends the variation at a 45° (or other) angle into the z-axis. Thus, a 45° resolution gauge, for example, weighs influence of the z-axis at an equal weight to the x or y axis because trigonometric projections are equal for the z-axis with either x, or y-depending on orientation. Other inclination angles, relative to the x-y plane, could be used to augment or diminish z effect versus, x or y.

The new 3D resolution gauge includes a series of groupings or segments of three-dimensional line pairs, all of the line pairs being oriented at a constant set acute angle, e.g. 45° (or other), relative to a reference x-y imaging plane. The repetition rate or frequency of the line pairs of respective groupings or segments of the series varies from highest density to lowest density corresponding to fine resolution and coarse resolution, respectively. Imaging of the series of groupings or segments of line pairs by the tomographic imaging system provides, in a single scan, a simultaneous visualization of combined effects of x-y in-plane resolution and slice thickness z direction resolution.

Each segment or grouping is preferably implemented by spaced apart fins or ramps (or other similar repetitive structures) located in spaced apart parallel planes, all oriented at a constant set acute angle relative to the reference x-y imaging plane. It can be noted that most tomographic imaging systems using square acquisition matrices (square pixels), e.g. 256×256, or 512×512, produce images with the same x and y resolution level; so that the segments or groupings can be aligned with either the x or the y axis, enabling the repetition rate to be basically one dimensional (x or y). In the event of a non-symmetric x,y resolution e.g. 256×512, the gauge can be moved from the x to the y alignment, while still showing the z-axis resolution effect.

The fins or ramps (or other similar repetitive structures) may comprise metal or other high contrast material embedded in a surrounding background material having a different, e.g. lower, absorption density than the fins or ramps. Alternatively, by using different materials, e.g. air and plastic, or different density plastics, the background material may have a higher absorption density than the fins or ramps. The fins or ramps may be connected by a common support element running along an edge of the fins or ramps The series of segments may be linearly arranged along the x axis, y axis or an intermediate axis of the x-y plane, across the test object, e.g. from lowest density/coarse resolution segment to highest density/fine resolution segment. Alternatively, the series of segments may be arranged or distributed in other patterns, e.g. a circular or octagonal or other arrangement, in the x-y plane, provided that all of the fins or ramps are oriented at the constant set acute angle relative to the x-y plane.

Advantageously, all of the ramps or fins may be oriented at a constant set angle of 45° to provide equal weighting of the x-y plane resolution contribution and the z direction resolution contribution to the resulting combined visualization. If desired, the constant set angle may differ from 45° to give more or less weight to z axis versus x-y plane resolution contributions in the resulting combined image or visualization, as created by the tomographic imaging system under test.

The resolution gauge of the present invention is applicable to all tomographic imaging systems, including but not limited to x-ray computed tomography (CT), magnetic resonance imaging (MR), nuclear medicine tomography including emission computed tomography such as positron emission tomography (PET) and single photon emission computed tomography (SPECT) as well as nuclear magnetic resonance (MRT) and other emerging hybrid techniques such as SPECT-CT, PET-CT, PET/MRI, as well as others.

Although amenable to quantitative analysis (in a manner similar to that described in commonly assigned U.S. Pat. No. 8,348,508 B2), the new resolution gauge advantageously provides a physician, clinician or other user of the tomographic imaging system with a single visual image, test and/or analysis of 3D (voxel) resolution which affords easy, immediate and intuitive understanding of image resolution simultaneously and effectively in 3 dimensions.

The new resolution gauge is designed to simultaneously visualize the combined effects of in-plane (x,y) resolution as well as slice thickness (z) resolution, and can reveal the way in which the actual CT resolution can be limited by the choice of reconstruction filter and/or the slice thickness or SSP (z) used for the acquisition. Likewise, phantoms incorporating the resolution gauge can be used in other CT acquisition strategies and reconstruction methods such as: direct 3D volume acquisition models, and multiplanar reconstruction (MPR) where different planes are resynthesized from acquired axial slices; or 3D reconstruction approaches such as cone beam reconstruction algorithms.

In a simplified embodiment, a single grouping of angled ramps of known varying density/frequency may be imaged to determine threshold image resolution in 3 dimensions. In another embodiment, a side by side pair of oppositely directed resolution gauges may be employed to resolve any in-plane misalignment of the test object.

The present invention further contemplates test objects and phantoms, test methods and apparatus all employing the new resolution gauge for evaluating performance of tomographic imaging devices. Examples of such utilization may be acquired from the description in commonly assigned U.S. Pat. No. 8,348,508 B2, the entire contents of which is hereby incorporated by reference herein.

The current invention also contemplates a method for evaluating performance of a tomographic imaging system that includes: imaging the three-dimensional gauge, in a single scan, with the tomographic imaging system; and viewing the simultaneous visualization for image resolution evaluation simultaneously in three dimensions, and/or image resolution evaluation by an automated process.

The method may further include a step of setting the common acute angle to selectively weight the slice thickness z direction resolution versus the x-y in-plane resolution effects of the simultaneous visualization. The common acute angle may be set to 45 degrees for equal weighting of the slice thickness z direction resolution and the x-y in-plane resolution effects in the simultaneous visualization.

Alternatively, the common acute angle may be set to less than 45 degrees to augment weight of the slice thickness z direction resolution, or set to more than 45 degrees to diminish weight of the slice thickness z direction resolution.

The method may further include: employing the image resolution evaluation to guide choice of a resolution filter and/or slice thickness in an image acquisition protocol; and/or using the three-dimensional resolution gauge in a direct 3D volume acquisition model and a multiplanar or 3D reconstruction.

BRIEF DESCRIPTION OF THE DRAWING FIGURES

Various embodiments of the invention will be described, in conjunction with the accompanying drawings, in which.

DETAILED DESCRIPTION

Figure 1:
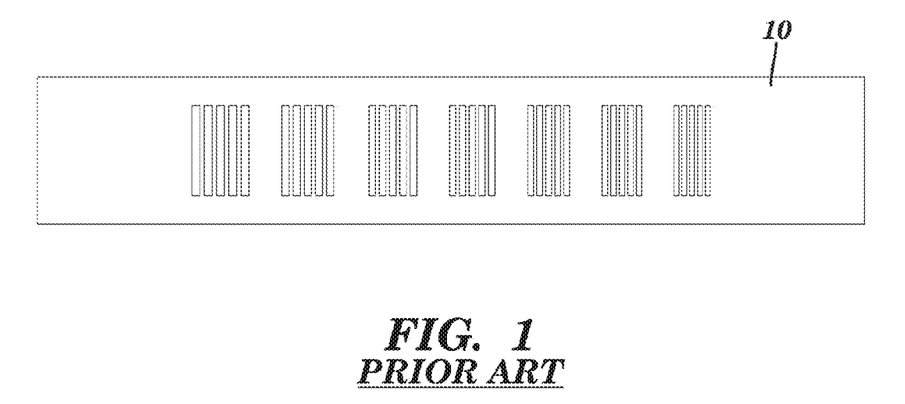
FIG. 1 is a top plan view of a conventional 2D in-plane resolution gauge.
Figure 2:
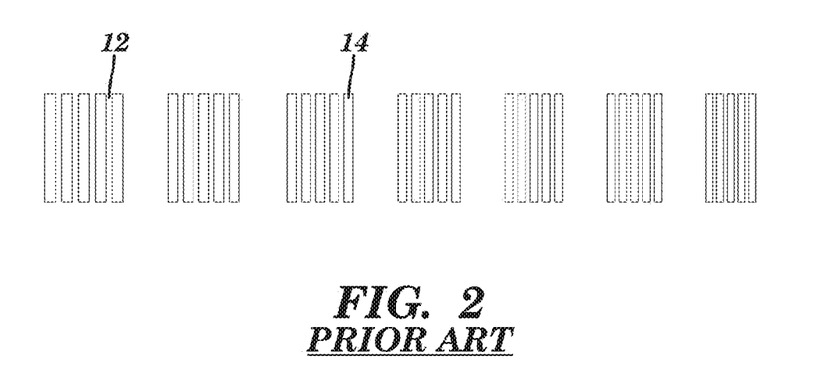
FIG. 2 is a schematic illustration of an arrangement of line pairs of the conventional 2D in-plane resolution gauge.

FIGS. 1 and 2 illustrate a conventional in-plane, 2-dimensional high resolution gauge 10. As one moves from left to right, it becomes more difficult to identify the white lines (spaces) 12 between the black lines (bars) 14. So basically, the better the in-plane or x-y imaging resolution, the finer the pattern that can be discerned. However, such in-plane gauges fail to consider z axis effects on image resolution in tomographic imaging systems.

Figure 3:
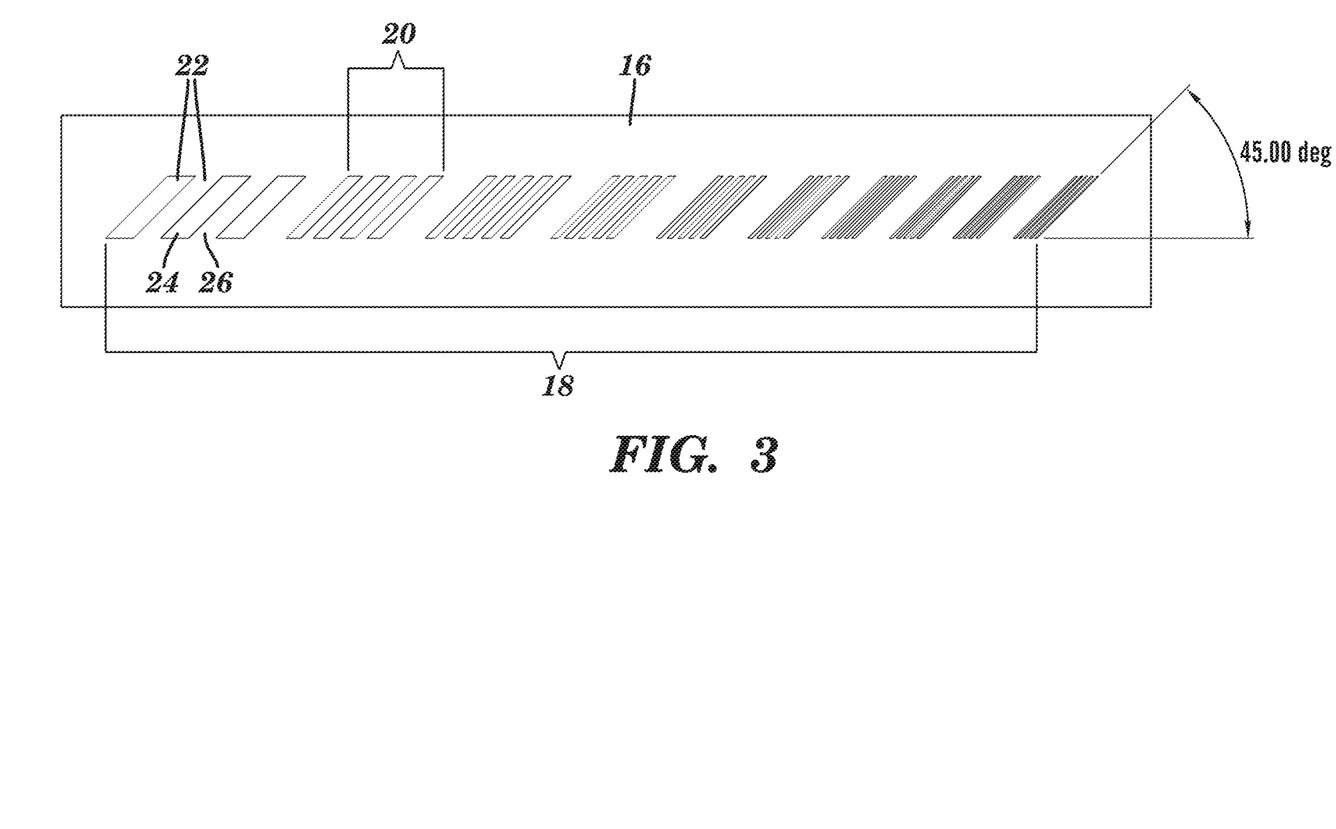
FIG. 3 is a side view of a 3D resolution gauge, in accordance with the present invention.

FIG. 3 is a schematic side view of an example of a 45° resolution gauge 16, constructed according to the principles of the present invention. The gauge includes a series 18 of segments or groupings 20 of 3-dimensional line pairs 22. Each grouping 20 is composed of angled fins or ramps 24, set at a common constant acute angle of 45°, in spaced apart parallel planes. Each line pair 22 comprises a single ramp 24 and an adjacent intermediate space 26. From one end to the other end of the gauge 16, e.g., from left to right in FIG. 3, the frequency of the ramps within the different segments or groupings increases.

Figure 4:
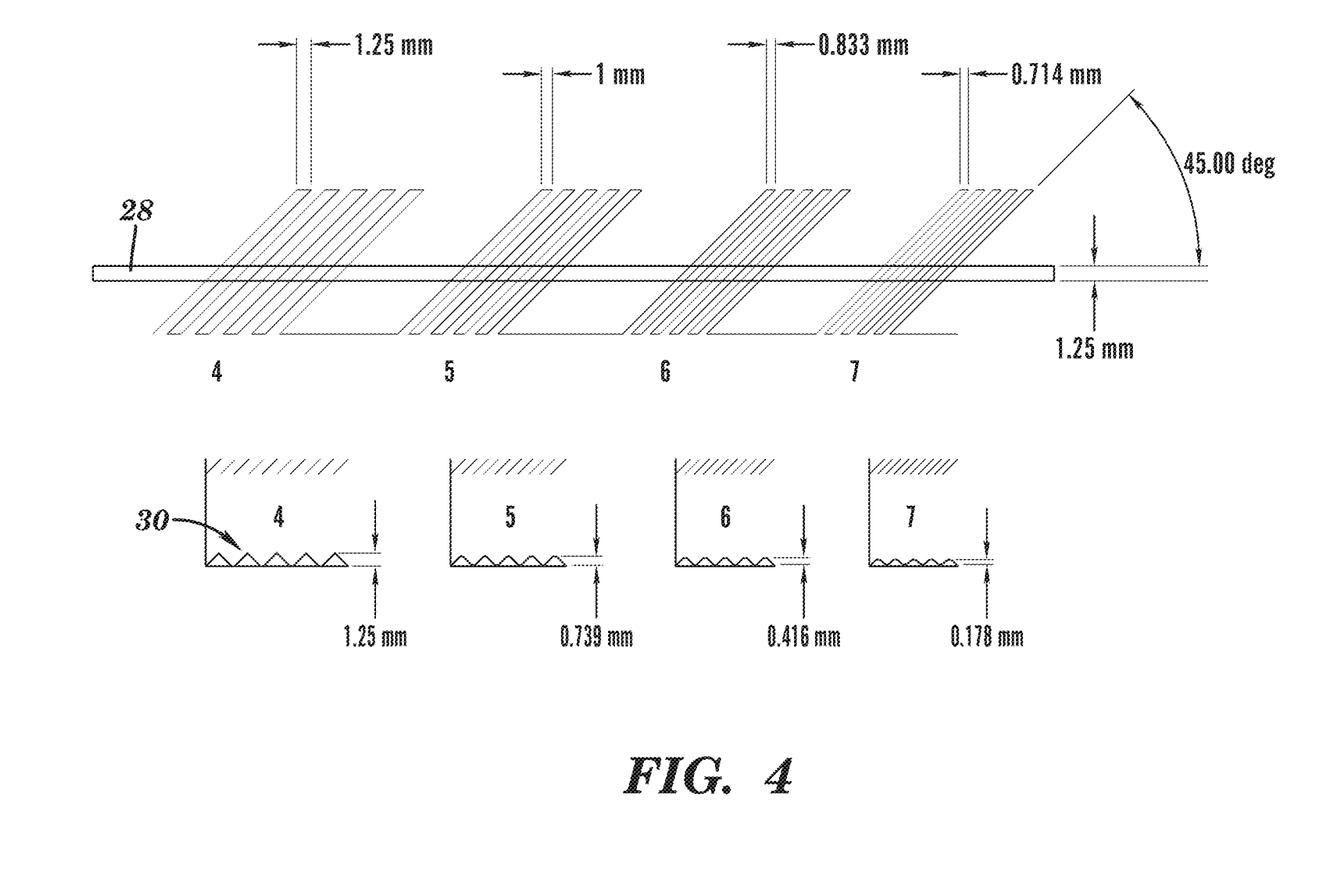
FIG. 4 shows a side view of several groupings (with 4-7 line pairs/cm) of angled ramps of one example of a 45° resolution gauge and related signal profiles, in accordance with the present invention.

FIG. 4 shows a schematic side view of several groupings (with, for example, 4-7 line pairs/cm) of angled ramps of one example of a 45° 3D resolution gauge and related signal profiles. A slice 28 through this resolution gauge would create triangular signal profiles as seen in the patterns 30 on the bottom of this figure. As the relative heights of the triangular peak decreases, less and less contrast is seen in the pattern. These patterns assume perfect x-y resolution; in the real world, the shapes of the blocks of these patterns would be rounded out as the x-y resolution declines. So if we widen the slice thickness z (1.25 mm in this figure) or reduce the x-y resolution, the patterns will flatten more and more. As one moves from left to right in FIG. 4, it becomes more difficult to identify the spaces between the bars. So basically, the better the in-plane x-y, and z direction imaging resolutions, the finer the pattern that can be discerned.

The dimensions shown in FIG. 4 are for illustrative purposes only, and the actual dimensions of the gauge, number, dimensions and spacing of the groupings, number, dimensions, spacing and frequency of the line pairs, as well as the set acute constant angle, may vary.

Figure 5:
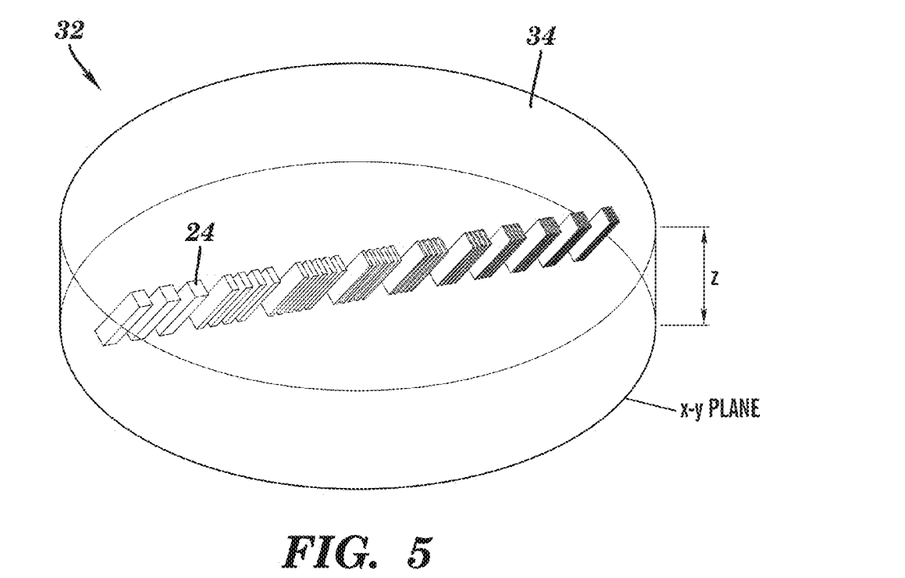
FIG. 5 is a perspective view of a 45° resolution gauge embedded in a test object of a phantom.

FIG. 5 illustrates a 45° resolution gauge embedded in a test object 32 of a phantom. The fins or ramps 24 (or other similar repetitive 3D structures) of the resolution gauge 16 may comprise metal, e.g., aluminum, or other high contrast material embedded in a surrounding background material 30, e.g., plastic, having a different e.g., lower absorption density than the fins or ramps. Alternatively, by using different materials, e.g. air and plastic, or different density plastics, the background material may have a higher absorption density than the fins or ramps.

The series of segments or groupings 18 of ramps or fins 24 may be linearly arranged along the x axis, y axis or an intermediate axis of the x-y plane, across the test object 32, e.g., from lowest density grouping to highest density grouping, as depicted in FIG. 5. Alternatively, the series of groupings may be arranged or distributed in other patterns, e.g., a circular or octagonal or other arrangement, in the x-y plane, provided that all of the fins or ramps are oriented at the constant set acute angle relative to the x-y plane.

In the illustrated embodiment, all of the fins or ramps 24 are oriented at a constant set angle of 45° to provide equal weighting of the x-y plane resolution contribution and the z direction resolution contribution to the resulting combined visualization. If desired, the constant set angle may differ from 45° to give more or less weight to z axis versus x-y plane resolution contributions in the resulting combined image or visualization, as created by the tomographic imaging system under test.

Figure 6:
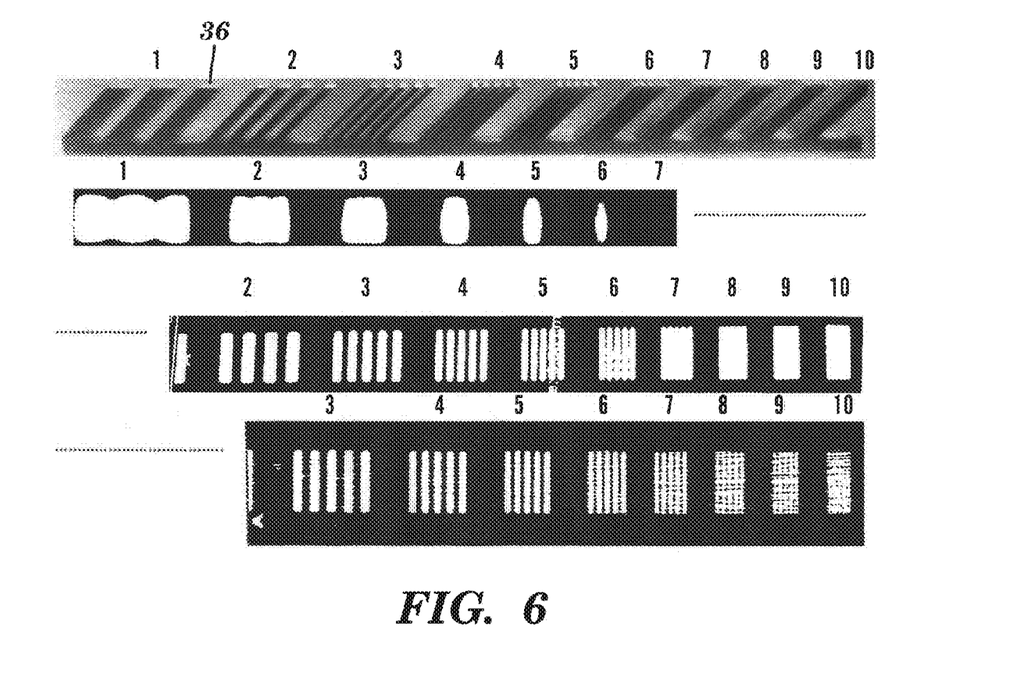
FIG. 6 illustrates an example of a 45° resolution gauge of the present invention, and the results of high resolution scans by a tomographic imaging system, with different slice thicknesses, of the 45° resolution gauge, resulting in different line pair visualization.

FIG. 6 illustrates an example of a 45° resolution gauge of the present invention, and the results of high resolution scans by a tomographic imaging system, with different slice thicknesses, of the 45° resolution gauge.

Examples are shown in the CT scans of FIG. 6 of the use of a 45° resolution gauge with a CT scanner. The cutoff of the 45° resolution gauge is shown for various acquisition protocols involving different spatial resolution filters and different slice thicknesses. The limitations of using in-plane high resolution filters (e.g., greater than 10 line pairs/cm for this example) when using a typical slice thickness of 0.6 to 10 mm are shown for a CT scanner.

The high resolution scans of FIG. 6 illustrate the effect of slice thickness on the 3D visualization provided by the resolution gauge of the present invention. When one scans the gauge with a CT system that has a high in-plane resolution, e.g., greater than 10 line pairs/cm, the resulting gauge pattern will be dominated by the slice thickness of the CT scanner. Note, typical CT scanners currently range from in-plane resolution levels from about 5 to 20 line pairs/cm (0.5 to 2 line pairs/mm), while typical slice thicknesses range from about 0.5 mm to 10 mm.

In the illustrated embodiment, the gauge ranges from 1-10 line pairs/cm, from left to right. The groupings of ramps or fins may be connected by a common support element 36 running along one edge of the fins or ramps. This particular gauge was scanned using an in-plane reconstruction filter that would normally show well in excess of 10 line pairs/cm (e.g. 13 line pairs/cm) using a conventional thin gauge where slice thickness would not affect the result.

The top image shows a photograph of the gauge;

In descending order, the second image shows a scan with the slice thickness of 10 mm, which should theoretically show a 0.5 line pairs/cm (fc=1/(2×10 mm) resolution bar based on domination of the slice thickness in terms of overall resolution. Note less than 1 line pairs/cm is seen.

The third image shows a scan with the slice thickness of 0.75 mm, which should theoretically show a 6.6 line pairs/cm (fc=1/(2×0.75 mm) resolution bar based on domination of the slice thickness in terms of overall resolution. Note about 6 line pairs/cm is visible.

The bottom image shows a scan with the slice thickness of 0.6 mm, which should theoretically show a 8 line pairs/cm (fc=1/(2×0.6 mm) resolution bar based on domination of the slice thickness in terms of overall resolution. Note about 8 line pairs/cm is seen.

Figure 7:
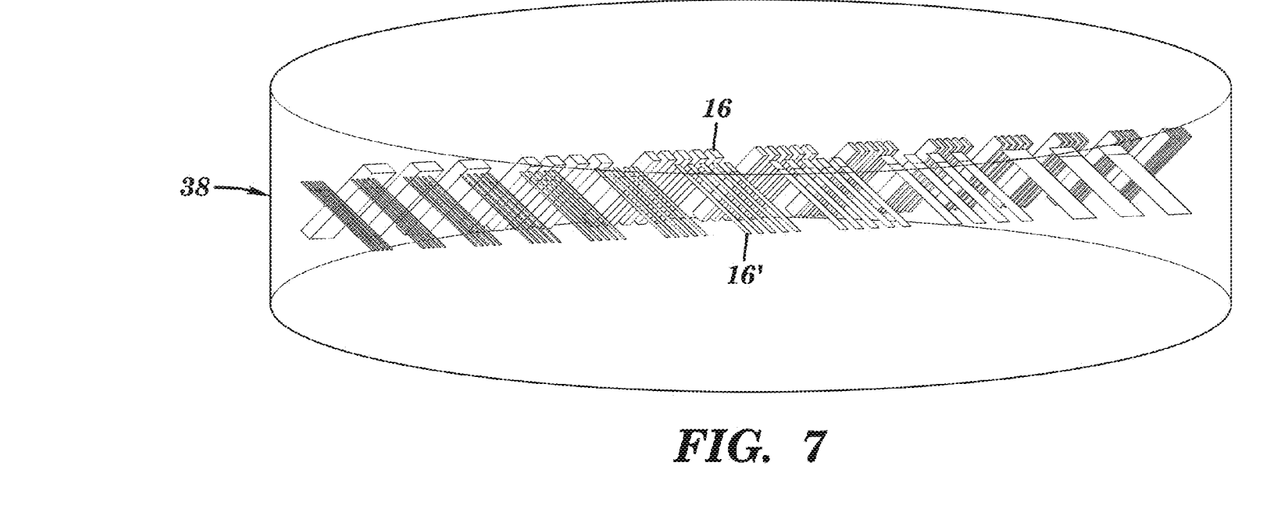
FIG. 7 provides a perspective view of another embodiment of a test object with a side by side pair of oppositely directed 45° resolution gauges.
Figure 8:
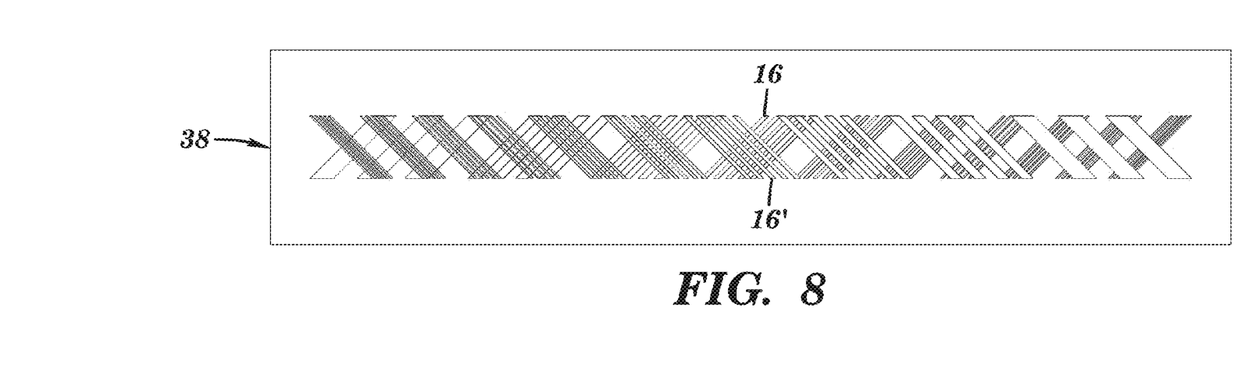
FIG. 8 is a side view of the resolution gauges of FIG. 7.

FIGS. 7 and 8 depict another test object 38 containing a side by side pair of oppositely directed 45° resolution gauges 16, 16' to eliminate errors due to poor in-plane alignment. This is helpful in the case wherein the CT slice is not entirely aligned in a scan angle sense, with a given x,y plane and thus the 45 degree angle might be augmented or diminished and this would be reflected in a slightly less angle on one gauge and enhanced on another. Thus the dual gauges could either provide an alignment test, and/or a way to average the results of the slightly increased and diminished gauges.

Figure 9:
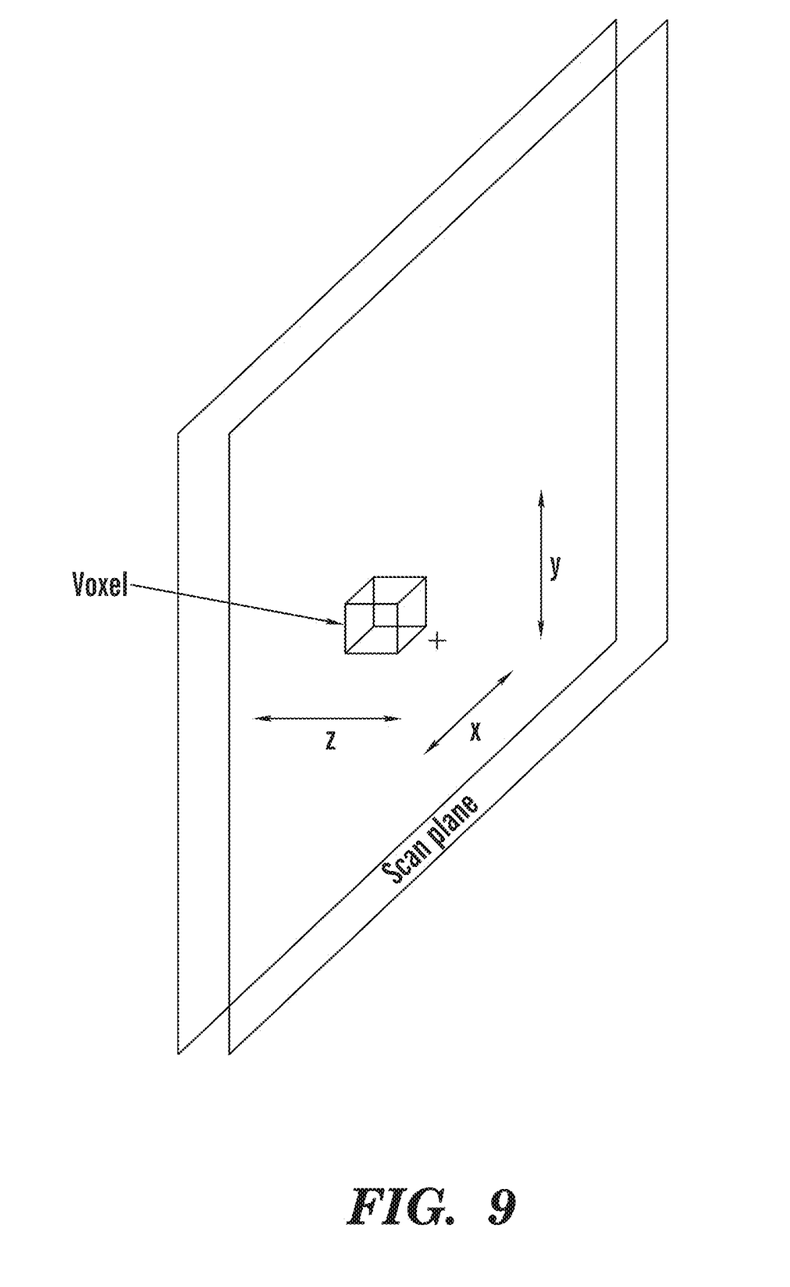
FIG. 9 illustrates a voxel volume for CT.

FIG. 9 illustrates a CT scan plane in an x-y orientation. Since the images in this plane are normally the result of a revolution of the tube around the body, the x and y resolutions are basically equal. The z direction is determined by the slice width, and is independent of the x-y in-plane resolution.

The data point in a CT image represents a voxel, whose in-plane (x,y) representation is a square pixel, and the z-axis representation is the slice thickness. Thus, we have a 3-D voxel element, ranging from a cube when x=y=z, to a rectangular volume when x=y≠z. Accordingly, for the cubic volume (x=y=z), by measuring x or y resolution, and z direction resolution, simultaneously, the combined resolution of the voxel can be evaluated for a sagittal or coronial image (y-z or x-y). Each axis has the same weight so a resolution gauge with a 45° angle, relative to the x-y image plane, is optimal.

However, for treatment planning for radiation therapy, z may only contribute, for example, ⅓ of the effect on the voxel and, therefore, a different set acute angel might better indicate the voxel volume resolution. By increasing the constant set acute angle above 45 degrees, the weight given to the slice thickness z direction resolution effect is diminished. Conversely, if the common constant acute angle is set to less than 45 degrees, weight of the slice thickness z direction resolution effect is enhanced.

Test methods and phantoms employing the new resolution gauge reveal useful information for 3D imaging on the combined effects of in-plane resolution and the slice thickness used in the acquisition or reconstruction process. These results can influence the appropriate choice of resolution filter and slice thickness in acquisition protocols.

These new approaches give the physician and clinician, for the first time, simultaneously, a qualitative (visual) measure of the combined effects of in-plane resolution and slice thickness used in the image acquisition or reconstruction process with a single scan of a single test object containing the new resolution gauge.

The invention claimed is:

1. A three-dimensional resolution gauge for evaluating performance of a tomographic imaging system, comprising: a series of groupings of three-dimensional line pairs, all of the line pairs being oriented at a common set acute angle relative to a reference x-y imaging plane, frequency of the line pairs of respective groupings of the series varying from highest density to lowest density corresponding to fine resolution and coarse resolution, respectively, wherein imaging of the series of groupings of line pairs by the tomographic imaging system provides, in a single scan, a simultaneous visualization of combined effects of x-y in-plane resolution and slice thickness z direction resolution, wherein each grouping comprises repetitive structures located in spaced apart parallel planes all oriented at said common set acute angle relative to the reference x-y image plane, and wherein the repetitive structures comprises fins or ramps.

2. The three-dimensional resolution gauge of claim 1, wherein the fins or ramps are connected by a common support element running along an edge of the fins or ramps.

3. The three-dimensional resolution gauge of claim 1, wherein the fins or ramps are embedded in a surrounding material having a different absorption density than the fins or ramps.

4. The three-dimensional resolution gauge of claim 3, wherein the fins or ramps comprise a metal or other contrast material embedded in a surrounding material having a lower absorption density than the fins or ramps.

5. The three-dimensional resolution gauge of claim 1, wherein the series of groupings are linearly arranged along an x-axis, y-axis or an intermediate axis of the reference x-y imaging plane, and extend progressively from the lowest density grouping to the highest density grouping.

6. The three-dimensional resolution gauge of claim 1, wherein the series of groupings are arranged in a non-linear pattern in the reference x-y imaging plane.

7. A phantom including the three-dimensional resolution gauge of claim 1 as a test object.

8. The phantom of claim 7, in combination with a tomographic imaging system.

9. The three-dimensional resolution gauge of claim 1, comprising: a first series of said groupings of line pairs; and a second oppositely directed series of said groupings of line pairs, adjacent said first series.

10. A phantom including the three-dimensional resolution gauge of claim 9 as a test object.

11. A method for evaluating performance of a tomographic imaging system, comprising:
imaging a three-dimensional resolution gauge comprising:
a series of groupings of three-dimensional line pairs, all of the line pairs being oriented at a common set acute angle relative to a reference x-y imaging plane, frequency of the line pairs of the respective groupings of the series varying from highest density to lowest density corresponding to fine resolution and course resolution, respectively, wherein the imaging of the series of groupings of line pairs by the tomographic imaging system provides, in a single scan, a simultaneous visualization of combined effects of x-y in-plane resolution and slice thickness z direction resolution, wherein each grouping comprises repetitive structures located in spaced apart parallel planes all orientated at said common set acute angle relative to the reference x-y imaging plane, and wherein the repetitive structure comprise fins or ramps, in a single scan, with the tomographic imaging system; and
viewing the simultaneous visualization for image resolution evaluation simultaneously in three dimensions, and/or image resolution evaluation by an automated process.

12. The method of claim 11, further comprising: setting the common acute angle to selectively weight the slice thickness z direction resolution versus the x-y in-plane resolution effects in the simultaneous visualization.

13. The method of claim 12, wherein the common acute angle is set to 45 degrees for equal weighting of the slice thickness z direction resolution and the x-y in-plane resolution effects in the simultaneous visualization.

14. The method of claim 12, wherein the common acute angle is set to less than 45° to augment weight of the slice thickness z direction resolution.

15. The method of claim 12, wherein the common acute angle is set to more than 45° to diminish weight of the slice thickness z direction resolution.

16. The method of claim 11, further comprising: employing the image resolution evaluation to guide choice of a resolution filter and/or slice thickness in an image acquisition protocol.

17. The method of claim 11, further comprising: using the three-dimensional resolution gauge in a direct 3D volume acquisition model and a multiplanar or 3D reconstruction.

18. A three-dimensional resolution gauge for evaluating performance of a tomographic imaging system, comprising:
a series of groupings of three-dimensional line pairs, all of the line pairs being oriented at a common set acute angle relative to a reference x-y imaging plane, frequency of the line pairs of respective groupings of the series varying from highest density to lowest density corresponding to fine resolution and coarse resolution, respectively, wherein imaging of the series of groupings of line pairs by the tomographic imaging system provides, in a single scan, a simultaneous visualization of combined effects of x-y in-plane resolution and slice thickness z direction resolution, and
wherein all of the line pairs are oriented at a common set acute angle of 45° relative to the reference x-y imaging plane to provide equal weighting to effects of x-y in-plane resolution and slice thickness z direction resolution in the simultaneous visualization.

* * * * *